United States Patent [19]

Wirth et al.

[11] 4,196,137

[45] Apr. 1, 1980

[54] PROCESS FOR THE PRODUCTION OF ORGANO-TIN COMPOUNDS

[75] Inventors: Hermann O. Wirth, Bensheim; Hermann W. Wehner, Zwingenberg; Eberhard Otto, Lindenfels, all of Fed. Rep. of Germany

[73] Assignee: Ciba-Geigy Corporation, Ardsley, N.Y.

[21] Appl. No.: 900,547

[22] Filed: Apr. 27, 1978

[30] Foreign Application Priority Data

May 6, 1977 [CH] Switzerland ................. 5707/77

[51] Int. Cl.$^2$ ............................................. C07F 7/22
[52] U.S. Cl. .................................................... 260/429.7
[58] Field of Search ....................................... 260/429.7

[56] References Cited

U.S. PATENT DOCUMENTS

| | | | |
|---|---|---|---|
| 3,412,122 | 11/1968 | Considine et al. | 260/429.7 |
| 3,440,255 | 4/1969 | Matsuda | 260/429.7 |
| 3,607,893 | 9/1971 | Reifenberg | 260/429.7 |
| 4,080,362 | 3/1978 | Hutton et al. | 260/429.7 X |
| 4,080,363 | 3/1978 | Hutton et al. | 260/429.7 X |
| 4,105,684 | 8/1978 | Hutton et al. | 260/429.7 |
| 4,130,573 | 12/1978 | Hutton et al. | 260/429.7 |

FOREIGN PATENT DOCUMENTS

2648107  2/1978  Fed. Rep. of Germany ........ 260/429.7

OTHER PUBLICATIONS

Chemical Abstracts, 65:5482h (1966).
Chemical Abstracts, 85, 109442b (1976).
Chemical Abstracts, 86, 44403b (1977).

*Primary Examiner*—Helen M. S. Sneed
*Attorney, Agent, or Firm*—Luther A. R. Hall

[57] ABSTRACT

Diorgano-tin dihalides containing functional groups in the organo groups are obtained in simple manner by the direct reaction of metallic tin with hydrogen chloride, hydrogen bromide or hydrogen iodide and an unsaturated nitrile, in the presence of water, water and alcohol, a carboxylic acid and/or alcohol.

16 Claims, No Drawings

PROCESS FOR THE PRODUCTION OF ORGANO-TIN COMPOUNDS

The present invention relates to a process for the production of carbofunctional organo-tin compounds.

Organo-tin compounds are of considerable economic interest as stabilisers for halogen-containing thermoplastics. Recently, carbofunctional organo-tin compounds have also been proposed for this purpose. There are various possibilities of producing such stabilisers.

For example, German Offenlegungsschrift No. 1,963,569 discloses in general terms that halostannic acid reacts in the presence of polar solvents with olefins which can contain functional groups. Acrylonitrile is cited by way of example. It has been found, however, that in this reaction the desired compound is obtained in only unsatisfactory yield. Moreover, only monoorgano-tin compounds can be produced by this process.

Monoorgano-tin compounds which contain a β-carbonylethyl group are also only obtained by a process described in German Offenlegungsschrift No. 2,540,210. They are produced by the reaction of tin dihalide with hydrogen halide and a corresponding olefin.

A similar process, but for the production of diorgano-tin compounds, is described in German Offenlegungsschrift No. 2,607,178. However, this process is restricted to those olefins which contain a carbonyl group in conjugation to the double bond, and it cannot be applied as a matter of course to other substituted vinyl compounds, for example nitriles.

There is a interest in economic processes for the production of carbofunctional diorgano-tin dihalides using easily obtainable starting compounds. It is the object of the present invention to provide such a process.

Accordingly, the invention provides a process for the production of organo-tin compounds of the formula

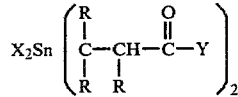

wherein
X represents a chlorine, bromine or iodine atom,
Y represents —OH, —NH$_2$ or —OR', in which R' represents a hydrocarbon group of aliphatic or aromatic character which can contain functional groups, and
R represents a hydrogen atom and/or alkyl, by the direct reaction of metallic tin with an olefin and hydrogen chloride, hydrogen bromide or hydrogen iodide, which process comprises reacting, as olefin, an unsaturated nitrile of the formula

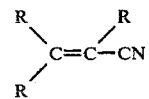

wherein R has the given meaning, in the presence of water or water and an alcohol R'—OH, or of a carboxylic acid or at least 6 moles of alcohol R'—OH per mole of nitrile,
wherein R' has the given meaning.

For predominantly economic reasons, X represents a chlorine atom. R is preferably hydrogen and/or methyl, especially hydrogen, this preference arising from the easily obtainable nitriles, viz. acrylonitrile, methacrylonitrile, crotonitrile and β-dimethylacrylonitrile.

Y preferably represents the group —OR'. R' as hydrocarbon group can be: linear or branched alkyl, unsubstituted or substituted cycloalkyl, cycloalkylalkyl, aryl and aralkyl, the preferred substitutent being alkyl which can contain functional groups. Cycloalkyl is preferably cyclohexyl, aryl is phenyl and aralkyl is benzyl. R' preferably contains 1 to 12 carbon atoms and represents especially cycloalkyl or linear or branched alkyl.

If R' is substituted by functional groups, these groups are for example hydroxyl, thiol, alkoxy, alkylthio, carboxyl and carbalkoxy.

Examples of R' are: methyl, ethyl, n- or iso-propyl, n-, iso- or tert-butyl, pentyl, hexyl, heptyl, 2-hexyl, 3-heptyl, octyl, 2-ethylhexyl, nonyl, decyl, undecyl, dodecyl, cyclopentyl, cyclohexyl, methylcyclohexyl, cyclohexylmethyl, methylcyclohexylmethyl, phenyl, methylphenyl, ethylphenyl, butylphenyl, octylphenyl, naphthyl, benzyl, methylbenzyl, octylbenzyl, α- or β-phenylethyl.

Examples of R' containing functional groups are: β-hydroxyethyl, β-mercaptoethyl, methoxyethyl, butoxyethyl, octoxyethyl, methylthioethyl, propylthioethyl, carboxymethyl, β-carboxyethyl and carboalkoxyalkyl, for example carbomethoxymethyl, carboethoxypropyl, carbobutoxyethyl, carbododecyloxymethyl.

In the process of the invention, the metallic tin can be used in different form, for example as powder, filings, granulate, tin dust or tin plate.

It is also possible to carry out the reaction in an excess of reactants as solvent or in an additional solvent. Suitable solvents are inert solvents, for example those with keto, ether, carboxylate, sulphoxide or sulphone functions. To avoid transesterification reactions, the ester function advantageously contains the radical of an alcohol which is used as reactant. Hydrocarbons, halogenated hydrocarbons and acid amides are also suitable, for example pentane, cyclohexane, benzene, toluene and dimethyl formamide.

In the reaction of the present invention, it is important that a carboxylic acid or at least 6 moles of alcohol are present in addition to the unsaturated nitrile, water or water and alcohol. The molar ratio of nitrile to water can be about 1:1 to about 1:2, in which case diorgano-tin halides with amide function (Y=NH$_2$) are obtained. If the ratio is greater than 1:2, preferably in water or aqueous HCl as reaction medium, diorgano-tin dihalides with carboxylic acid function are obtained.

By using nitrile, water and alcohol in the molar ratio of about 1:1, diorgano-tin dihalides with ester function Y=OR' are obtained. Diorgano-tin halides with amide function are also obtained by using nitrile and carboxylic acid in the molar ratio of at least about 1:1 (the carboxylic acid can be the reaction medium), accompanied by the formation of carboxylic anhydrides or carboxylic halides or CO on using formic acid. By using nitrile and alcohol in the molar ratio of at least about 1:6 (the alcohol can also be the reaction medium), diorgano-tin dihalides with ester function are obtained.

In this last-mentioned process, low molecular, readily volatile alcohols are advantageously used, especially aliphatic and cycloaliphatic alcohols containing 1 to 12, preferably 1 to 6, carbon atoms, in order that the ethers or halogenated hydrocarbons which have formed can be easily removed from the reaction mixture. Aliphatic, cyclo-aliphatic and aromatic carboxylic acids can be used. They contain preferably 1 to 12, especially 1 to 6, carbon atoms, in order to be able to remove the carboxylic anhydrides and carboxylic halides easily. Examples are benzoic acid, oxalic acid and, in particular, formic acid, acetic acid or propionic acid.

The reaction temperature is in general between −30° and +100° C., preferably between 20° and 50° C. The reaction is advantageously carried out under normal pressure or slight excess pressure.

The procedure is that hydrogen halide, especially HCl, is introduced into the reaction vessel which contains the tin and the reactants, with or without solvent.

It is however also possible to charge the reaction vessel with the tin in the solvent and to add the reactants and hydrogen halide gas simultaneously. In this case it is advantageous to proceed in accordance with the countercurrent principal, by means of which it is also possible to carry out the process continuously.

The process of the present invention affords valuable organo-tin compounds in high yields in simple and economic manner and under very mild reaction conditions. Easily obtainable and cheap products can be used as starting materials. In addition, surprisingly few divalent tin compounds are formed during the reaction.

No problems are encountered in isolating the desired diorgano-tin compounds. However, it is possible to carry out the reaction such that mixtures of such diorgano-tin compounds with the corresponding monoorgano-tin compounds are obtained. These mixtures can contain up to 50% by weight and more of monoorganotin compound.

The organo-tin compounds obtained according to the present invention can be used as biocides or catalysts for the production of polyurethane. However, they are especially suitable for use as intermediates for organo-tin stabilisers for stabilising halogen-containing thermoplastics. Further details relating to this use are described in German Offenlegungsschrift No. 2,607,178.

The invention is described in more detail by the following Examples in which the parts are by weight.

EXAMPLE 1

A three-necked flask equipped with stirrer, reflux cooler and thermometer is charged with 118 parts of tin granules and 74 parts of butanol. With stirring, a flow of dry HCl gas is introduced at 40°–50° C. and simultaneously a solution of 106 parts of acrylonitrile and 36 parts of water in 200 parts of n-butanol are added dropwise. The tin has reacted quantitatively after 6 hours. Ammonium chloride (108 parts) formed by saponification of the nitrile is removed from the reaction mixture by filtration. The residue consists of 33 parts of $SnCl_2$ and 253 parts of organo-tin compound, $Cl_2Sn(CH_2—CH_2—COOC_4H_9)_2$, which additionally contains a small amount of the corresponding monoorgano-tin compound, $(Cl_3SnCH_2CH_2—COOC_4H_9)$.

EXAMPLE 2

A three-necked flask equipped with stirrer, reflux cooler and bubble counter is charged at 20° C. with 7 parts of tin powder, 26.5 parts of acrylonitrile and 9 parts of water in 50 parts of dimethoxy ethane. With stirring, a flow of dry hydrogen chloride gas is passed through the mixture and is so regulated that absorption just occurs. The reaction temperature is between 30° and 40° C. After about 2 hours, the tin has reacted virtually quantitatively. Volatile constituents are stripped off in a high vacuum, yielding as residue a wax-like substance which consists of 85.5 mol% of the amide of the formula

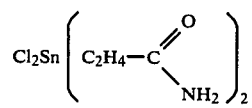

and 14.2 mol% of the amide of the formula

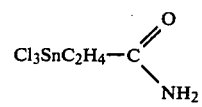

EXAMPLE 3

23.7 parts of tin powder, 21.2 parts of acrylonitrile and 90 parts of absolute ethanol are reacted by saturation with HCl gas at 35°–45° C. The tin has dissolved in the course of 3 hours and HCl saturation occurs after 6 hours. Volatile constituents are stripped off, yielding a crystalline product whose main component consists of

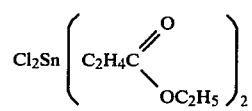

as confirmed by $^1$NMR spectroscopy.

The probable reaction course is illustrated by the empirical equation

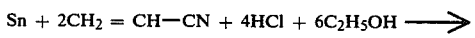
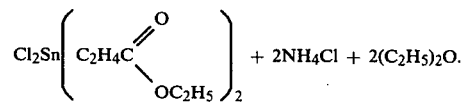

EXAMPLE 4

29.7 parts of tin filings, 26.5 parts of acrylonitrile and 30 parts of glacial acetic acid in 50 parts of diglyme as solvent are reacted while introducing HCl gas. After 5 hours at 40° C., 96% of the tin has reacted. Volatile constituents are stripped off in vacuo, yielding a crystalline residue which consists of

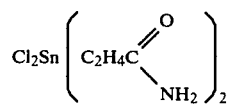

and a small amount of

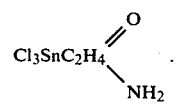

The likely reaction course is illustrated by the equation:

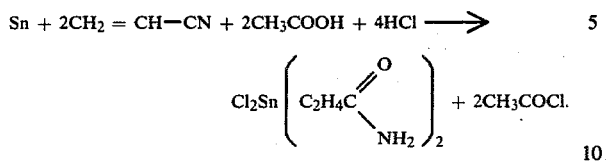

If the reaction is carried out in 100 parts of glacial acetic acid as reaction medium, 88% of the tin has reacted after 7 hours using tin granules. $^1$NMR spectroscopy confirms that the amount of

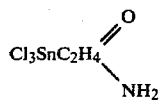

has increased.

EXAMPLE 5

29.7 parts of tin filings, 26.5 parts of acrylonitrile, and 9 parts of H$_2$O in 50 parts of chloroform as solvent are reacted while introducing HCl gas. The reaction time is 2 hours and the reaction temperature is 40° C. Volatile constituents are stripped off in vacuo, affording a solid residue from which a mixture of

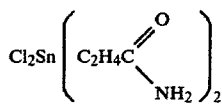

and

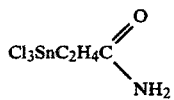

is isolated in 96% yield. (Detection by $^1$NMR spectroscopy).

EXAMPLE 6

A three-necked flask equipped with stirrer, reflux cooler and bubble counter is charged at room temperature with 23.7 parts of tin powder, 0.4 parts of acrylonitrile and 100 parts of concentrated HCl. HCl gas is introduced until the mixture is saturated (about 4 hours), whilst the temperature rises to about 60° C. Volatile constituents are removed in vacuo, affording a wax-like residue in which no SN$^{2+}$ can be detected. Accordingly, the tin has reacted quantitatively to give the organo-tin compound. The NMR spectrum shows the wax-like residue to be Cl$_2$SN(C$_2$H$_4$COOH)$_2$.

The chemical displacement of the carboxyl protons is deuterised dimethyl sulphoxide to trimethylsilane is 6.7 ppm.

The carboxylated diorgano-tin dihalides are preferably produced in concentrated HCl or water as reaction medium. However, the reaction can also be carried out in aqueous organic solvents.

What is claimed is:

1. A process for the production of organotin compounds of the formula

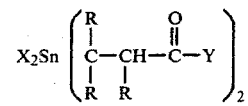

wherein
X represents a chlorine, bromine or iodine atom,
Y represents —OH, —NH$_2$ or —OR' in which R' represents a hydrocarbon group of aliphatic or aromatic character, or said groups substituted by a hydroxyl, thiol, alkoxy, alkylthio, carboxyl or carboalkoxy group, and
R is selected from the group consisting of a hydrogen atom and alkyl, which comprises reacting, at −30° C. to +100° C., metallic tin with hydrogen chloride, hydrogen bromide or hydrogen iodide and an unsaturated nitrile of the formula

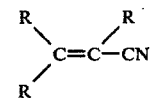

in a reactant medium selected from the group consisting of water, aqueous hydrochloric acid, water and alcohol, carboxylic acid, and alcohol with the proviso that when the reactant medium is alcohol the molar ratio of alcohol to nitrile is at least about 6:1.

2. A process according to claim 1 wherein X is a chlorine atom.

3. A process according to claim 1, wherein Y is the group —OR'.

4. A process according to claim 1, wherein the hydrocarbon group contains 1 to 12 carbon atoms.

5. A process according to claim 4, wherein the hydrocarbon group R' is linear or branched alkyl or cycloalkyl.

6. A process according to claim 1, wherein the unsaturated nitrile is acrylonitrile, methacrylonitrile, crotonitrile or β-dimethylacrylonitrile.

7. A process according to claim 1, wherein an excess of water, alcohol, aqueous HCl or carboxylic acid is used as reaction medium.

8. A process according to claim 1, wherein the reaction is carried out at a temperature of 20° to 50° C., and under normal or slight excess pressure.

9. A process according to claim 1 wherein R is selected from the group consisting of a hydrogen atom and methyl.

10. A process according to claim 1 wherein R is hydrogen.

11. A process according to claim 1 wherein the reactant medium is water, the molar ratio of water to nitrile is about 1:1 to 2:1, and a compound where Y is NH$_2$ is formed.

12. A process according to claim 1 wherein the reactant medium is water, the molar ratio of water to nitrile is greater than 2:1, and a compound where Y is OH is formed.

13. A process according to claim 1 wherein the reactant medium is aqueous hydrochloric acid, and a compound where Y is OH is formed.

14. A process according to claim 1 wherein the reactant medium is water and alcohol of formula R'OH the molar ratio of water to alcohol to nitrile is about 1:1:1, and a compound where Y is OR' is formed.

15. A process according to claim 1 wherein the reactant medium is a carboxylic acid, the molar ratio of said acid to nitrile is at least about 1:1, and a compound where Y is NH$_2$ is formed.

16. A process according to claim 1 wherein the reactant medium is an alcohol R'OH, the molar ratio of alcohol to nitrile is at least about 6:1, and a compound where Y is OR' is formed.

* * * * *